(12) United States Patent
Duran et al.

(10) Patent No.: US 6,869,968 B1
(45) Date of Patent: Mar. 22, 2005

(54) 2-(3H)-OXAZOLONE DERIVATIVES AND THEIR USE AS COX-2 INHIBITORS

(75) Inventors: Carles Puig Duran, Barcelona (ES); Ferran Pujol Noguera, Barcelona (ES); Dolors Fernandez Forner, Barcelona (ES)

(73) Assignee: Allmirall Prodesfarma S.A., Barcelona (ES)

( * ) Notice: Subject to any disclaimer, the term of this patent is extended or adjusted under 35 U.S.C. 154(b) by 505 days.

(21) Appl. No.: 09/158,966

(22) Filed: Sep. 21, 1998

Related U.S. Application Data

(63) Continuation of application No. PCT/EP97/01386, filed on Mar. 19, 1997.

(30) Foreign Application Priority Data

Mar. 21, 1996 (ES) ................................................ 9600685

(51) Int. Cl.⁷ ........................ A61K 31/42; C07D 263/04
(52) U.S. Cl. ........................................ 514/376; 548/232
(58) Field of Search ........................... 514/376; 548/232

(56) References Cited

U.S. PATENT DOCUMENTS

| 5,380,738 A | 1/1995 | Norman et al. .............. 514/374 |
| 5,866,596 A * | 2/1999 | Sartori et al. ................ 514/376 |

FOREIGN PATENT DOCUMENTS

| EP | 0 329 070 A1 | 8/1989 |
| EP | 0 745 596 A1 | 4/1996 |
| EP | WO 97/34882 | 9/1997 |
| FR | 96 11188 | 3/1998 |
| FR | WO 98/11080 | 3/1998 |
| WO | WO94/27980 | 12/1994 |

* cited by examiner

*Primary Examiner*—Brenda Coleman
(74) *Attorney, Agent, or Firm*—Venable LLP; Marina V. Schneller; Keith G. Haddaway

(57) ABSTRACT

The invention relates to 2-(3H)-oxazolone derivatives. They may be used as COX-2 inhibitors. The compounds may be used in the treatment of colorectal cancer.

52 Claims, No Drawings

2-(3H)-OXAZOLONE DERIVATIVES AND THEIR USE AS COX-2 INHIBITORS

CROSS-REFERENCE TO RELATED APPLICATIONS

This application is a continuation of International Patent Application No. PCT/EP97/01386, filed on Mar. 19, 1997 and published on Sep. 25, 1997 as International Publication WO 97/34882; that international application, in turn, claims priority of Spanish Patent Application No. 96 00685 filed Mar. 21, 1996. Each of said international application and said Spanish applications are relied upon and are expressly incorporated by reference herein.

This invention relates to new therapeutically useful 2-(3H)-oxazolone derivatives, to processes for their preparation and to pharmaceutical compositions containing them.

The mechanism of action of non steroidal anti-inflammatory drugs is believed to be the inhibition of the enzyme cyclooxygenase (COX) and consecutively the conversion of the arachidonic acid into prostaglandines. The identification of cyclooxygenase-1 (COX-1) and cyclooxygenase-2 (COX-2) isoenzymes led to the hypothesis that the inhibition, particularly selective inhibition, of COX-2 would reduce inflammation without the side effects of classical non steroidal anti-inflammatory drugs, gastric and renal toxicity.

In accordance with this hypothesis, we have now found that certain 2-(3H)-oxazolone derivatives inhibit COX-2 and selectively inhibit COX-2 in preference to COX-1. These derivatives have efficacy and good tolerance in the treatment of COX-2 mediated diseases, such as inflammation, pain, fever and asthma, and fewer side effects, such as ulcerogenic activity.

Accordingly the present invention provides a 2-(3H)-oxazolone compound of formula (I):

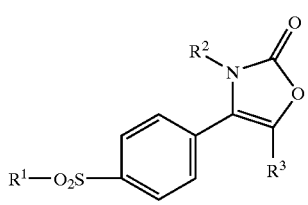

(I)

wherein:
R$^1$ is an alkyl or —NR$^4$R$^5$ group, wherein R$^4$ and R$^5$ each independently is hydrogen or an alkyl or benzyl group;
R$^2$ is a naphthyl (preferably 2-naphthyl) tetrahydronaphthyl, unsubstituted phenyl or phenyl group substituted by from 1 to 3 halogen atoms (preferably chlorine or fluorine) or alkyl, hydroxy, alkoxy or trifluoromethyl groups; and
R$^1$ is hydrogen or an alkyl group.

The alkyl groups and moieties, such as in the alkoxy groups, mentioned in relation to the groups R$^1$ to R$^5$ are usually "lower" alkyl, that is containing up to 6 and particularly up to 4 carbon atoms, the hydrocarbon chain being branched or straight. A preferred alkyl group or moiety is methyl.

The substituents on the phenyl ring may be in any position. For example a single substituent may be on position 2, 3 or 4; or two substituents may be on positions 2 and 4 or 3 and 4.

Preferred compounds of formula (I) are those wherein R$^1$ is an alkyl or amino group, R$^2$ is a phenyl group substituted by one or two halogen atoms (especially chlorine or fluorine) and R$^3$ is hydrogen.

The substituents on the phenyl group represented by R$^2$ may be the same or different.

Of outstanding interest are:
3-(4-fluorophenyl)-4-(4-methylsulphonylphenyl)-2-(3H)-oxazolone, 3-(2-fluorophenyl)-4-(4-aminosulphonylphenyl)-2-(3H)-oxazolone, 3-(3,4-dichlorophenyl)-4-(4-aminosulphonylphenyl)-2-(3H)-oxazolone and 3-(2,4-difluorophenyl)-4-(4-aminosulphonylphenyl)-2-(3H)-oxazolone.

The present invention also provides processes for preparing a compound of formula (I) which depend on the definition of R$^1$.

The present invention provides a process for the preparation of a compound of formula (I) wherein R$^1$ is an alkyl or —NR$^4$R$^5$ group in which R$^4$ and R$^5$ are other than hydrogen, viz. a 2-(3H)-oxazolone derivative of formula (II):

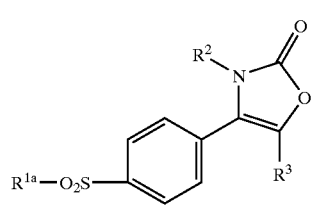

(II)

wherein R$^{1a}$ is an alkyl or —NR$^{4a}$R$^{5a}$ group in which R$^{4a}$ and R$^{5a}$ each independently is an alkyl or benzyl group, and R$^2$ and R$^3$ are as defined above which comprises reacting a carbamate Of formula (V):

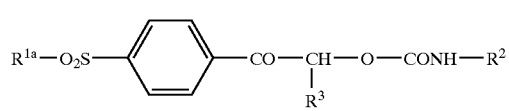

(V)

wherein R$^{1a}$, R$^2$ and R$^3$ are as defined above with anhydrous acetic acid.

The carbamate of formula (V) may be obtained, for example, by reacting a phenacyl alcohol of formula (III):

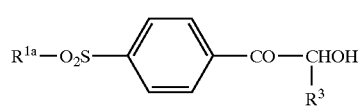

(III)

wherein R$^{1a}$ and R$^3$ are as defined above, with an isocyanate of formula (IV):

OCN—R$^2$ (IV)

wherein R$^2$ is as defined above.

The reaction between the phenacyl alcohol of formula (III) and the isocyanate of formula (IV) may be carried out by heating a mixture of these two starting materials, optionally in the presence of an organic solvent such as toluene or xylene, at a temperature of from 80° C. to 200° C.

The carbamate of formula (V) may also be prepared by reacting a thio derivative of formula (VI):

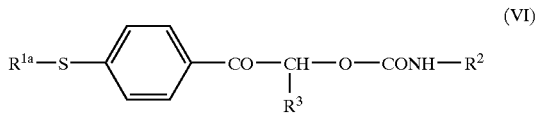
(VI)

wherein $R^{1a}$, $R^2$ and $R^3$ are as defined above, with an oxidizing agent, preferably magnesium monoperoxyphthalate or 3-chloroperoxybenzoic acid. The reaction is preferably carried out in an organic solvent such as a mixture of methylene chloride with methanol or ethanol, at a temperature of from 10° C. to 40° C.

The carbamate of formula (V) may be isolated after each process by known methods. The carbamate may be heated to a temperature of from 80° C. to 120° C. with an excess of anhydrous acetic acid to give the compound of formula (II).

The present invention also provides a process for the preparation of a compound of formula (I) wherein $R^1$ is an alkyl group, viz. a 2-(3H)-oxazolone derivative of formula (VII):

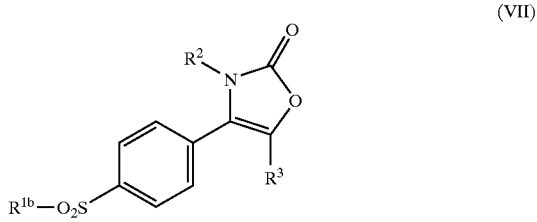
(VII)

wherein $R^{1b}$ is an alkyl group and $R^2$ and $R^3$ are as defined above by reacting a mercapto derivative of formula (VIII):

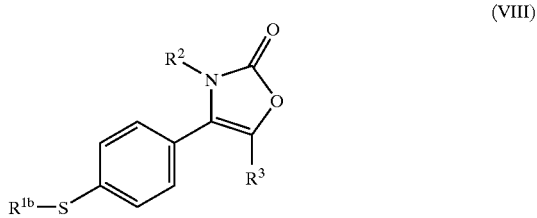
(VIII)

wherein $R^{1b}$, $R^2$ and $R^3$ are as defined above with an oxidizing agent, preferably with magnesium monoperoxyphthalate or 3-chloroperoxybenzoic acid.

The reaction between the mercapto derivative of formula (VIII) and the oxidizing agent is preferably carried out, as previously disclosed for the compound of formula (VI), in an organic solvent such as a mixture of methylene chloride with methanol or ethanol, at a temperature of frog 10° C. to 40° C.

The present invention additionally provides a process for the preparation of a compound of formula (I) wherein $R^1$ is a —$NR^4R^5$ group, viz. the 2-(3H)-oxazolone derivative of formula (IX):

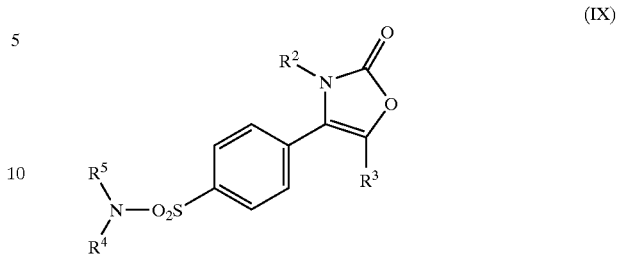
(IX)

wherein $R^2$, $R^3$, $R^4$ and $R^5$ are as defined above by reacting a chlorosulphonyl derivative of formula (XI):

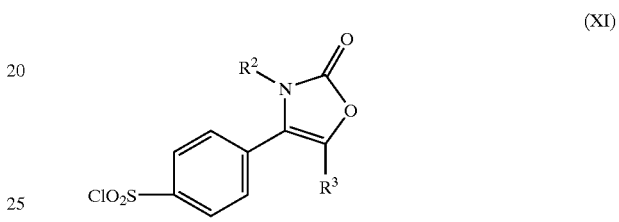
(XI)

wherein $R^2$ and $R^3$ are as defined above with an amine of formula (XII):

$R^4$—NH—$R^5$ (XII)

wherein $R^4$ and $R^5$ are as defined above.

This reaction is preferably carried out at a temperature of from 10° C. to 40° C.

The chlorosulphonyl derivative of formula (XI) may, for example, be prepared by reacting a compound of formula (X):

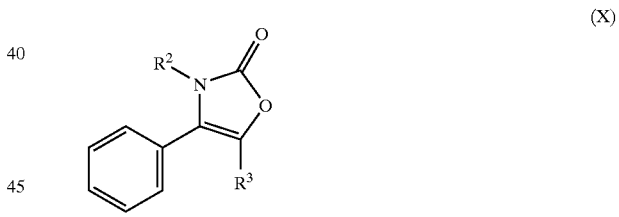
(X)

wherein $R^2$ and $R^3$ are as defined above with chlorosulphonic acid, preferably at a temperature of from 80° C. to 120° C.

The present invention further provides a process for the preparation of a compound of formula (I) wherein $R^1$ is a —$NR^4R^5$ group wherein $R^4$ and $R^5$ are hydrogen, viz, the 2-(3H)-oxazolone derivative of formula (XIII):

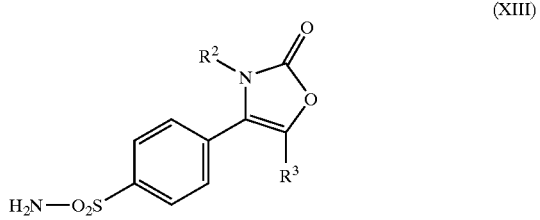
(XIII)

wherein $R^2$ and $R^3$ are as defined above by debenzylation of the corresponding compound of formula (IX) wherein $R^4$ and $R^5$ are as defined above with the proviso that at least one, preferably both, of $R^4$ and $R^5$ is a benzyl group, for example the 2-(3H)-oxazolone derivative of formula (XIV):

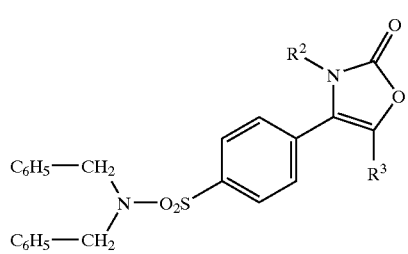

(XIV)

wherein $R^2$ and $R^3$ are as defined above.

The debenzylation is preferably carried out with an excess of trifluoroacetic, sulphuric or methanesulphonic acid at a temperature of from 0° C. to 120° C.

The intermediates of formulae (III) and (VI) used in the preparation of the compounds of the invention may be prepared by methods disclosed in the literature, for example, in M. F. Saettone, J. Org. Chem. 31, p. 1959 (1966).

The intermediate compounds of formulae (VIII) and (X) may be prepared by the same process disclosed for the preparation of compounds of formula (II), with the appropriate starting materials.

The following biological tests and data further illustrate this invention.

For the whole-cell COX-1 and COX-2 assays, stock solutions ($10^{-3}$M) of the drugs were dissolved in 50% dimethylsulphoxide, and further dilutions were done with medium. Drug vehicle, at concentrations employed, did not affect enzyme activities.

Inhibition of Cyclooxygenase-1 (COX-1) Activity in Human Platelets

Platelets were isolated from peripheral human blood obtained from healthy donors who had denied taking any non-steroidal anti-inflammatory drugs during at least the previous week. The blood was anticoagulated with 2 mg/ml sodium EDTA and centrifuged at 180 g for 10 min. at room temperature to obtain platelet-rich plasma. The platelet-rich plasma was centrifuged at 2000 g for 20 min. at 4° C. to obtain a platelet pellet. Cells were washed twice with PBS without $Ca^{2-}$ and $Mg^{2-}$ and resuspended to $5 \times 10^7$ cells with Hank's balanced salt solution (HBSS). Platelets ($10^7$) were preincubated with the drugs for 15 min. at 37° C. and incubations were continued for a further 15 min. in the presence of 50 μM arachidonic acid. The production of tromboxane $B_2$ in response to arachidonic acid was measured in the supernatants using a solid-phase immunoassay (ELISA). The results are expressed as the mean of the $IC_{50}$ values obtained from three independent experiments.

Inhibition of Cyclooxygenase-2 (COX-2) Activity in HUV-EC-C Cell Line

The human endothelial cell line HUV-EC-C expresses selectively cycloxygenase-2 isoenzyme after treatment with phorbol 12-myristate 13-acetate (PMA) (Miralpeix et al., "Agents and Actions", 44: S274(1995)). HUV-EC-C cells were grown on Ham's F12K medium containing 10% fetal bovine serum, 100 μg/ml heparin and 50 μg/ml Endothelial Cell Growth Supplement (ECGS). Experiments were performed with HUV-EC-C passage 19–27. Cells ($2 \times 10^4$) were seeded onto 96-well plates and made quiescent by removing the growth factor for 48 h before the initiation of the experiments. Quiescent HUV-EC-C cells were treated with 50 nM TPA for 6 h at 37° C. to induce the COX-2 isoenzyme. The cultured medium was then changed and cells were incubated with drugs for 30 min. at 37° C. Arachidonic acid (50 μM) was then added, and the cells were incubated for a further 30 min. The production of prostaglandine $E_2$ in response to arachidonic acid was measured in the supernatants using a solid-phase immunoassay (ELISA). The results are expressed as the mean of the $IC_{50}$ values obtained from three independent experiments.

Ulcerogenic Activity

Animals: Male Wistar (Interfauna, U.K., Ltd.) weighing about 120–150 g were used. They were maintained on a 12:12 hour light-dark cycle (lights on at 7:00 a.m.) at room temperature (22±1° C.). The animals were fasted for 18 h prior to the experiment with free access to drinking water.

Procedure: Experiments were performed from 9 to 17 h. The compounds were administered by-the oral route and the animals were sacrificed 6 hours after drugs dosage. The stomach of each rat was removed, opened and gently washed. The macroscopic severity of the erosions was assessed using a parametric scale (Cosen and Mazure), evaluating the number and size of the ulcers in the glandular stomach. Thus, each stomach was classified with an index lesion and compared with the gastrolesivity induced by ketorolac 100 mg/kg p.o., used as a positive standard. The treatments were randomized in each experiment.

Anti-Inflammatory Activity (Adjuvant Arthritis)

Male Wistar rats weighing 175–200 g with free access to food and water were used. On day 0, the animals received an intraplantar injection of a suspension of *Mycobacterium tuberculosis* in paraffin oil (0.5 mg/rat) on the left hind paw. A group of 8 nonarthritic control rats were injected with paraffin oil alone. On days 11 and 14 after induction of arthritis, the volume of the hind paw of each rat was measured using a water plehysmograph. Animals whose paw volumes increased during that time were selected. Rats were distributed into groups of 8 having equal mean paw volumes and an approximately equal standard deviation.

Test compounds were administered p.o. once daily for 7 days (days 14–20). Nonarthritic and arthritic control rats received vehicle alone for 7 days. The hind paw volumes were measured 20 h after the last dose (on day 21). The body weight was determined every second day.

The results are expressed as the percentage of inhibition of inflammation (paw volume) for each treatment group, considering both the arthritic and nonarthritic vehicle controls. The ANOVA test was used for statistical studies.

Drugs

For the whole-cell COX-1 and COX-2 assays stock solutions ($10^{-3}$ M) of the drugs wer dissolved in 50% dimethylsulphoxide, and further dilutions were done with medium. The drug vehicle, at the concentrations employed, did not affect the enzyme activities.

For the in vivo assays all drugs were administered in vehicle (0.1% Tween 80+0.5% methylcellulose in distilled water) in a volume of 5 ml/kg.

Results

The results obtained from the biological assays are shown in Tables 1, 2 and 3.

TABLE 1

Inhibition of COX-1 and COX-2

| COMPOUND (*) | COX-1 (μM) () | COX-2 (μM) () | Ratio COX-1:COX-2 |
|---|---|---|---|
| Indomethacin | 0.047 | 0.15 | 0.3 |
| 6 | 127 | 3.2 | 39.6 |
| 9 | >100 | 0.11 | >909 |
| 12 | >100 | 0.4 | >250 |

TABLE 1-continued

Inhibition of COX-1 and COX-2

| COMPOUND (*) | COX-1 ($\mu$M) () | COX-2 ($\mu$M) () | Ratio COX-1:COX-2 |
|---|---|---|---|
| 16 | 27.9 | 0.008 | 3487 |
| 17 | >100 | 0.03 | >3333 |
| 18 | 1.5 | 0.53 | 2.8 |
| 20 | 3.5 | 0.06 | 58.3 |
| 23 | 4.6 | 0.26 | 17.7 |
| 26 | 22.6 | 0.0096 | 2354 |
| 27 | 8.9 | 0.1 | 89 |

(*) See structures in Table 4. Indomethacin is 1-(4-chlorobenzoyl)-5-methoxy-2-methylindole-3-acetic acid, a non steroidal anti-inflammatory drug.
(**) Results expressed as $IC_{50}$ values.

TABLE 2

Anti-inflammatory activity

| COMPOUND | % Inhibition (dose, mg/kg) |
|---|---|
| Indomethacin | 64 (1) |
| 6 | 52 (3) |
| 18 | 63 (1) |
| 20 | 67 (1) |
| 23 | 62 (1) |
| 26 | 65 (1) |
| 27 | 64 (1) |

TABLE 3

Ulcerogenic activity

| COMPOUND | $UD_{50}$ (mg/kg) |
|---|---|
| Indomethacin | 17 |
| 6 | >100 |
| 20 | >100 |
| 26 | >100 |
| 27 | >100 |

As shown in Table 1, the compounds of formula (I) are selective and potent COX-2 inhibitors. We have found that the compounds of the examples are more effective in inhibiting COX-2 activity than they are inhibiting COX-1 activity, whereas the reference compound indomethacin is a potent and selective COX-1 inhibitor. Due to their low COX-1 activity, the compounds of formula (I) present an important anti-inflammatory activity (see Table 2) and the benefit of significantly less harmful side effects than the non-steroidal anti-inflammatory drugs commonly used (e.g. gastrointestinal toxicity (see Table 3), renal side-effects, reduced effect on bleeding times and asthma induction in aspirin-sensitive subjects).

The present invention provides a compound of formula (I) for use in a method of treatment of the human or animal body by therapy, in particular for the treatment of pain, fever or inflammation, to inhibit prostanoid-induced smooth muscle contraction or for the prevention of colorectal cancer.

The present invention also provides the use of a compound of formula (I) in the manufacture of a medicament for the treatment of pain, fever or inflammation, to inhibit prostanoid-induced smooth muscle contraction or for the prevention of colorectal cancer.

The compounds of formula (I) are useful for relief of pain, fever and inflammation of a variety of conditions including rheumatic fever, symptoms associated with influenza or other viral infections, common cold, low back and neck pain, dysmenorrhoea, headache, toothache, sprains and strains, myositis, neuralgia, synovitis, bursitis, tendinitis, injuries, following surgical and dental procedures and arthritis including rheumatoid arthritis, osteoarthritis, gouty arthritis, spondyloarthopathies, systemic lupus erythematosus and juvenile arthritis. They may also be used in the treatment of skin inflammation disorders such as psoriasis, eczema, burning and dermatitis. In addition, such compounds may be used for the prevention of colorectal cancer.

The compounds of formula (I) will also inhibit prostanoid-induced smooth muscle contraction and therefore may be used in the treatment of dysmenorrhoea, premature labour, asthma and bronchitis.

The compounds of formula (I) can be used as alternative to conventional non-steroidal anti-inflammatory drugs, particularly where such non-steroidal anti-inflammatory drugs may be contra-indicated such as the treatment of patients with gastrointestinal disorders including peptic ulcers, gastritis, regional enteritis, ulcerative colitis, diverticulitis, Crohn's disease, inflammatory bowel syndrome and irritable bowl syndrome, gastrointestinal bleeding and coagulation disorders, kidney disease (e.g. impaired renal function), those prior to surgery or taking anticoagulants, and those susceptible to non steroidal anti-inflammatory drugs induced asthma.

The compounds can further be used to treat inflammation in diseases such as vascular diseases, migraine headaches, periarteritis nodosa, thyroiditis, aplastic anaemia, Hodgkin's disease, scleroderma, type I diabetes, myasthenia gravis, sarcoidosis, nephrotic syndrome, Behcet's syndrome, polymyositis, hypersensitivity, conjunctivitis, gingivitis and myocardial ischaemia.

Compounds of the present invention are inhibitors of cyclooxygenase-2 enzyme and are thereby useful to treat the cyclooxygenase-2 mediated diseases enumerated above.

The present invention furthermore provides a pharmaceutical composition which comprises, as active ingredient, at least one 2-(3H)-oxazolone derivative of formula (I) and a pharmaceutically acceptable carrier or diluent. Preferably the compositions are in a form suitable for oral, topical, inhalation, rectal, transdermal, nasal or parenteral administration. The pharmaceutically-acceptable carriers or diluents which are admixed with the active compound or compounds to form the compositions of this invention are well known per se and the actual excipients used depend inter alia on the intended method of administration of the compositions. Compositions of this invention are preferably adapted for administration per os.

In this case, the compositions for oral administration may take the form of tablets, capsules, lozenges or effervescent granules or liquid preparations such as elixirs, syrups or suspensions, all containing one or more compounds of the invention. Such preparations may be made by methods well known in the art, for instance by mixing the 2-(3H)-oxazolone derivative of formula (I) with the pharmaceutically acceptable carrier or diluent.

The diluents which may be used in the preparation of the compositions include those liquid and solid diluents which are compatible with the active ingredient, together with colouring or flavouring agents if desired. Tablets or capsules may conveniently contain between 10 and 500 mg and preferably from 15 to 100 mg of active ingredient. The compounds may also be incorporated into pellets coated with appropriate natural or synthetic polymers known in the art to produce sustained release characteristics or incorporated with polymers into tablet form to produce the same characteristics.

The liquid compositions adapted for oral use may be in the form of solutions, suspensions or aerosols. The solutions may be aqueous-alcoholic solutions of a 2-(3H)-oxazolone in association with, for example, sucrose or sorbitol to form a syrup. The suspensions may comprise an insoluble or microencapsulated form of an active compound of the invention in association with water and other acceptable solvents together with a suspending agent or flavouring agent.

Compositions for inhalation administration may be in the form of solutions, suspensions or micronized powder, contained in an appropriate inhaler.

Compositions for parenteral injection may be prepared in the form of microemulsions or microsuspensions in water or an appropriate parenteral injection fluid.

In human therapy, the doses of the 2-(3H)-oxazolone derivatives depend on the desired effect and duration of the treatment; adult doses are generally between 15 mg and 500 mg per day. In general the physician will decide the posology taking into account the age and weight of the patient being treated.

The 2-(3H)-oxazolone derivatives of formula (I) may be used in a method of treatment of any of the above conditions which comprises administering to a subject in need of such treatment an effective amount of the derivative of formula (I).

The following Examples further illustrate the invention.

EXAMPLE 1 a) A mixture of 4-methylsulphonylphenacyl alcohol (3 g; 0.014 moles) m.p. 133–135° C., and 4-fluorophenyl isocyanate (5 ml; 0.044 moles) was stirred for 1 hour at 100° C. After cooling, the resulting solid was treated with diisopropyl ether (30 ml), collected by filtration and washed with a 10% mixture of methanol in diethyl ether. 4-methylsulphonylphenacyl N-(4-fluorophenyl) carbamate (3.5 g) was obtained as a white solid, m.p. 198–200° C. (d).

b) A solution of the above compound (3 g; 0.0085 moles) in anhydrous acetic acid (30 ml) was boiled under reflux for 8 hours. The solvent was removed in vacuo the residue crystallized from a mixture of acetonitrile (10 ml) and diisopropyl ether (20 ml) and then recrystallized from a mixture of ethanol and methylene chloride. 3-(4-fluorophenyl)-4-(4-methylsulfonylphenyl)-2-(3H)-oxazolone (1.9 g), was obtained, m.p. 170–172° C. This compound has another crystalline form with m.p. 152–153° C.

EXAMPLE 2 a) A solution of 4-methylthiophenacyl alcohol (1 g; 5.5 mmoles) and 4-bromophenyl isocyanate (1.08 g; 5.4 mmoles) in anhydrous xylene (10 ml) was boiled under reflux for 5 hours. Then the reaction mixture was cooled and the solid was filtered off and washed with diisopropyl ether to give 4-methylthiophenacyl N-(4-bromophenyl) carbamate as a white solid (1.8 g).

b) A solution of the above carbamate (1.8 g; 4.7 mmoles) in anhydrous acetic acid (18 ml) was boiled under reflux for 16 hours, the solvent removed in vacuo and the residue treated with acetone. The resulting white solid was filtered off and 3-(4-bromophenyl)-4-(4-methylthiophenyl)-2-(3H)-oxazolone (1 g) was obtained.

c) To a solution of the above compound (1 g; 2.7 mmoles) in methanol (3 ml) and methylene chloride (17 ml), magnesium monoperoxyphtalate hexahydrate (2.13 g; 4.3 mmoles) was slowly added, and the mixture stirred at room temperature for 2 hours. Then it was washed with 4M sodium bicarbonate aqueous solution, dried ($Na_2SO_4$) and the solvent removed under reduced pressure. The residue was recrystallized from methylene chloride-ethanol to give 3-(4-bromophenyl)-4-(4-methylsulfonylphenyl)-2-(3H)-oxazolone (0.63 g), m.p. 217–219° C.

EXAMPLE 3 a) A solution of phenacyl N-(4-fluorophenyl) carbamate (9.6 g; 35 mmoles) in anhydrous acetic acid (96 ml) was boiled under reflux for 16 hours. The solvent was removed under reduced pressure and a solid crystallized, which was collected by filtration and washed with diethyl ether. 3-(4-fluorophenyl)-4-phenyl-2-(3H)-oxazolone (7.8 g) was obtained, m.p. 145–147° C.

b) A mixture of the above compound (4 g; 15.7 mmoles) and chlorosulphonic acid (2.1 ml; 31.6 mmoles) was heated at 100° C. for 4 hours, cooled and then poured into iced-water. The precipitated solid was extracted with ethyl acetate, dried ($Na_2SO_4$) and the solvent removed in vacuo. To the residue, concentrated ammonium hydroxide (40 ml) was added, stirred at room temperature for half an hour and extracted with methylene chloride. The organic solution was dried ($Na_2SO_4$) the solvent removed under reduced pressure and the residue recrystallized from ethanol. 3-(4-fluorophenyl)-4-(4-aminosulfonylphenyl)-2-(3H)-oxazolone (0.89 g) was obtained, m.p. 211–213° C.

EXAMPLE 4 a) A solution of 4-(N,N-dibenzylaminosulfonyl) phenacyl N-(3,4-dichlorophenyl) carbamate (2.6 g; 4.46 mmoles) in anhydrous acetic acid (25 ml) was boiled under reflux for 6 hours. The solvent was removed under reduced pressure and the obtained oil was treated with diethyl ether. 3-(3,4-dichlorophenyl)-4-[4-(N,N dibenzylaminosulfonyl)phenyl]-2-(3H)-oxazolone crystallized (2.0 g), m.p. 128–130° C.

b) A solution of the above compound (2 g; 3.54 mmoles) in methanesulfonic acid (15 ml) was stirred at 100° C. for half an hour. The reaction mixture was poured into iced-water, the precipitated solid collected by filtration, and then treated with ethanol. The insoluble solid was filtered off and the solution was passed through a chromatography column containing silica gel and methylene chloride-methanol 95:5 as eluent. 3-(3.4-dichlorophenyl)—4—(4—aminosulfonylphenyl-Y—-2-(3H)-oxazolone (0.9 g) was obtained, m.p. 158–161° C.

Other 2-(3H)-oxazolone derivatives of formula (I) in Table 4 were prepared according to the processes disclosed in these Examples, but with the appropriate starting materials.

TABLE 4

$$\text{(I)}$$

Structure: R¹—O₂S—C₆H₄— attached to oxazolone ring with R² on N, R³ at 5-position, C=O at 2-position.

| Compound | R¹ | R² | R³ | Method Example | m.p. ° C. |
|---|---|---|---|---|---|
| 1 | H₃C | C₆H₅ | H | 1 | 207–210 |
| 2 | " | 4H₃C—C₆H₄ | " | " | 213–214 |
| 3 | " | 3H₃C—C₆H₄ | " | " | 195–197 |
| 4 | " | 2F—C₆H₄ | " | " | 186–187 |
| 5 | " | 3F—C₆H₄ | " | 2 | 138–139 |
| 6 | " | 4F—C₆H₄ | " | 1, 2 | 170–172 |
| 7 | " | 3Cl—C₆H₄ | " | 1 | 177–178 |
| 8 | " | 4Cl—C₆H₄ | " | 1 | 220–221 |
| 9 | " | 4Br—C₆H₄ | " | 2 | 217–219 |
| 10 | " | 4F₃C—C₆H₄ | " | 1 | 189–190 |
| 11 | " | 3Cl, 4H₃CO—C₆H₃ | " | 1 | 154–156 |
| 12 | " | 2, 4diF—C₆H₃ | " | 1 | 155–156 |
| 13 | " | 3, 4diF—C₆H₃ | " | 1 | 177–178 |
| 14 | " | 3Cl, 4F—C₆H₃ | " | 1 | 175–177 |
| 15 | " | 2, 4diCl—C₆H₃ | " | 1 | 199–200 |
| 16 | " | 3, 4diCl—C₆H₃ | " | 1 | 197–199 |
| 17 | " | 2-naphthyl | " | 1 | 222–223 |
| 18 | H₂N | 4F—C₆H₄ | " | 3 | 211–213 |
| 19 | " | 3Cl, 4F—C₆H₃ | " | 4 | 247–249 |
| 20 | " | 3, 4diCl—C₆H₃ | " | 4 | 158–161 |
| 21 | (C₆H₅—CH₂)₂N | 3Cl, 4F—C₆H₃ | " | 1 | 128–130 |
| 22 | H₃C | 4F—C₆H₄ | H₃C | 1 | 205–206 |
| 23 | H₂N | 4Cl—C₆H₄ | H | 4 | 211–212 |
| 24 | " | 4Cl, 3F—C₆H₃ | " | " | 186–187 |
| 25 | " | 3Cl—C₆H₄ | " | " | 176–177 |
| 26 | " | 2F—C₆H₄ | " | " | 178–179 |
| 27 | " | 2, 4diF—C₆H₃ | " | " | 190–192 |
| 28 | H₃C—NH | " | " | " | 136–138 |
| 29 | C₆H₅—CH₂—N—CH₃ | " | " | 1 | 125–127 |
| 30 | (H₃C)₂N | " | " | " | 157–159 |

The following Examples illustrate pharmaceutical compositions according to the present invention and procedures for their preparation.

EXAMPLE 5

10,000 Tablets each containing 50 mg of 3-(4-chlorophenyl-4-(4-methylsulfonyl-phenyl)-2-(3H)-oxazolone (active ingredient) were prepared from the following formulation:

| | |
|---|---|
| Active ingredient | 500 g |
| Microcrystalline cellulose | 390 g |
| Spray dried Lactose | 1.990 g |
| Carboxymethyl starch | 80 g |
| Sodium stearyl fumarate | 20 g |
| Colloidal silicon dioxide | 20 g |

Procedure

All the powders were passed through a screen with an aperture of 0.6 mm, then mixed in a suitable mixer for 20 minutes and compressed into 300 mg tablets using 9 mm discs and flat bevelled punches. The disintegration time of the tablets was about 3 minutes.

EXAMPLE 6

100,000 capsules each containing 100 mg of 3-(4-fluorophenyl)-4-(4-methylsulfonylphenyl)-2-(3H)-oxazolone (active ingredient) were prepared from the following formulation:

| | |
|---|---|
| Active ingredient | 10 kg |
| Lactose monohydrate | 20 kg |
| Corn starch | 2 kg |
| Magnesium stearate | 0.4 kg |
| Colloidal silicon dioxide | 0.2 kg |

Procedure

The above ingredients were sieved through a 60-mesh sieve, and were loaded into a suitable mixer and filled into 100,000 gelatine capsules.

What is claimed is:

1. A 2-(3H)-oxazolone compound of formula (I):

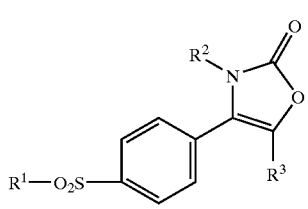

(I)

wherein:
R$^1$ is an alkyl or —NR$^4$R$^5$ group, wherein R$^4$ and R$^5$ each independently is hydrogen or an alkyl or benzyl group;
R$^2$ is a naphthyl, tetrahydronaphthyl, unsubstituted phenyl or phenyl group substituted by from 1 to 3 halogen atoms or alkyl, hydroxy, alkoxy or trifluoromethyl groups; and
R$^3$ is hydrogen or an alkyl group.

2. A compound according to claim 1 wherein R$^2$ is a 2-naphthyl group, phenyl group or a phenyl group substituted by 1 or 2 halogen atoms or alkyl, alkoxy or trifluoromethyl groups.

3. A compound according to claim 1 wherein the alkyl groups or moieties contain from 1 to 6 carbon atoms.

4. A compound according to claim 1 wherein R$^1$ is a methyl group or an amino group.

5. A compound according to claim 1 wherein R$^3$ is a hydrogen atom or a methyl group.

6. A compound according to claim 1 wherein R$^3$ is a hydrogen atom.

7. A compound according to claim 1 wherein R$^2$ is a phenyl group substituted by one or two halogen atoms or methyl groups.

8. A compound according to any one of claims 1 to 7 wherein R$^2$ is a phenyl group substituted by a single substituent at the 3- or 4-position.

9. A compound according to any one of claims 1, 3, 4, 5, or 6 wherein R$^2$ is a phenyl group substituted by two halogen atoms at positions 2 and 4 or 3 and 4.

10. A compound according to claim 1, selected from the group consisting of 3-(4-fluorophenyl)-4-(4-methylsulphonylphenyl)-2-(3H)-oxazolone; 3-(2-fluorophenyl)-4-(4-aminosulphonylphenyl)-2-(3H) oxazolone; 3-(3,4-dichlorophenyl)-4-(4-aminosulphonylphenyl)-2-(3H)oxazolone; and 3-(2,4-difluorophenyl)-4-(4-aminosulphonylphenyl)-2-(3H)-oxazolone.

11. A process for the preparation of a compound of formula (I) as defined in claim 1 which comprises:

a) when R$^1$ is an alkyl or NR$^4$R$^5$ group in which R$^4$ and R$^5$ are other than hydrogen, reacting a carbamate of formula (V):

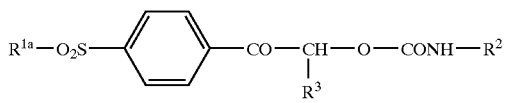

(V)

wherein R$^2$ and R$^3$ are as defined in claim 1 and R$^{1a}$ is an alkyl or NR$^{4a}$R$^{5a}$ group wherein R$^{4a}$ and R$^{5a}$ each independently is an alkyl or benzyl group with anhydrous acetic acid;

b) when R$^1$ is an alkyl group, reacting a mercapto derivative of formula (VIII):

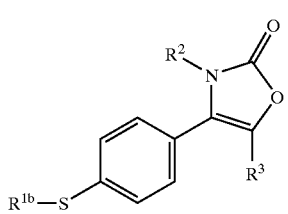

(VIII)

wherein R$^2$ and R$^3$ are as defined in claim 1 and R$^{1b}$ is an alkyl group with an oxidizing agent;

c) when R$^1$ is a NR$^4$R$^5$ group wherein R$^4$ and R$^5$ are as defined in claim 1, reacting a chlorosulphonyl derivative of formula (XI):

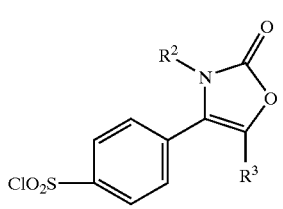

(XI)

wherein R$^2$ and R$^3$ are as defined in claim 1 with an amine of formula (XII):

R$^4$—NH—R$^5$ (XII)

wherein R$^4$ and R$^5$ are as defined in claim 1; or d) when R$^1$ is a —NR$^4$R$^5$ group wherein R$^4$ and R$^5$ are hydrogen, debenzylating the corresponding compound of formula (IX):

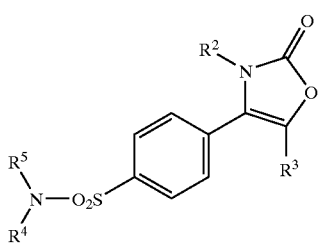

(IX)

wherein R$^2$, R$^3$, R$^4$ and R$^5$ are as defined in claim 1 with the proviso that at least one of R$^4$ and R$^5$ is a benzyl group.

12. A pharmaceutical composition which comprises, as active ingredient, at least one compound of formula (I) as defined in claim 1 and a pharmaceutically acceptable carrier or diluent.

13. A 2-(3H)-oxazolone compound of formula (I):

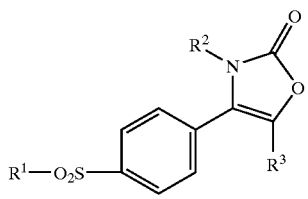

wherein $R^1$, $R^2$ and $R^3$ are defined as follows

| $R^1$ | $R^2$ | $R^3$ |
|---|---|---|
| $H_3C$ | $C_6H_5$ | H |
| $H_3C$ | $4H_3C—C_6H_4$ | H |
| $H_3C$ | $3H_3C—C_6H_4$ | H |
| $H_3C$ | $2F—C_6H_4$ | H |
| $H_3C$ | $3F—C_6H_4$ | H |
| $H_3C$ | $4F—C_6H_4$ | H |
| $H_3C$ | $3Cl—C_6H_4$ | H |
| $H_3C$ | $4Cl—C_6H_4$ | H |
| $H_3C$ | $4Br—C_6H_4$ | H |
| $H_3C$ | $4F_3C—C_6H_4$ | H |
| $H_3C$ | $3Cl,4H_3CO—C_6H_3$ | H |
| $H_3C$ | $2,4diF—C_6H_3$ | H |
| $H_3C$ | $3,4diF—C_6H_3$ | H |
| $H_3C$ | $3Cl,4F—C_6H_3$ | H |
| $H_3C$ | $2,4diCl—C_6H_3$ | H |
| $H_3C$ | $3,4diCl—C_6H_3$ | H |
| $H_3C$ | 2-naphthyl | H |
| $H_2N$ | $4F—C_6H_4$ | H |
| $H_2N$ | $3Cl,4F—C_6H_3$ | H |
| $H_2N$ | $3,4diCl—C_6H_3$ | H |
| $(C_6H_5—CH_2)_2N$ | $3Cl,4F—C_6H_3$ | H |
| $H_3C$ | $4F—C_6H_4$ | $H_3C$ |
| $H_2N$ | $4Cl—C_6H_4$ | H |
| $H_2N$ | $4Cl,3F—C_6H_3$ | H |
| $H_2N$ | $3Cl—C_6H_4$ | H |
| $H_2N$ | $2F—C_6H_4$ | H |
| $H_2N$ | $2,4diF—C_6H_3$ | H |
| $H_3C{-}NH{-}$ | $2,4diF—C_6H_3$ | H |
| $C_6H_5{-}CH_2{-}N(CH_3){-}$ | $2,4diF—C_6H_3$ | H |
| $(H_3C)_2N$ | $2,4diF—C_6H_3$ | H. |

14. A pharmaceutical composition which comprises, as an active ingredient, at least one compound as defined in claim 8 and a pharmaceutically acceptable carrier or diluent.

15. A pharmaceutical composition which comprises, as an active ingredient, at least one compound as defined in claim 9, and a pharmaceutically acceptable carrier or diluent.

16. A pharmaceutical composition which comprises, as an active ingredient, at least one compound as defined in claim 13 and a pharmaceutically acceptable carrier or diluent.

17. A method of treating pain comprising administering to a human or animal patient in need of said treatment, an effective amount of a compound as defined in any one of claims 1 to 7.

18. A method of treating pain comprising administering to a human or animal patient in need of said treatment, an effective amount of a compound as defined in claim 8.

19. A method of treating pain comprising administering to a human or animal patient in need of said treatment, an effective amount of a compound as defined in claim 9.

20. A method of treating pain comprising administering to a human or animal patient in need of said treatment, an effective amount of a compound as defined in claim 13.

21. A method of treating fever comprising administering to a human or animal patient in need of said treatment, an effective amount of a compound as defined in any one of claims 1 to 7.

22. A method of treating fever comprising administering to a human or animal patient in need of said treatment, an effective amount of a compound as defined in claim 8.

23. A method of treating fever comprising administering to a human or animal patient in need of said treatment, an effective amount of a compound as defined in claim 9.

24. A method of treating fever comprising administering to a human or animal patient in need of said treatment, an effective amount of a compound as defined in claim 13.

25. A method of treating inflammation administering to a human or animal patient in need of said treatment, an effective amount of a compound as defined in any one of claims 1 to 7.

26. A method of treating inflammation comprising administering to a human or animal patient in need of said treatment, an effective amount of a compound as defined in claim 8.

27. A method of treating inflammation comprising administering to a human or animal patient in need of said treatment, an effective amount of a compound as defined in claim 9.

28. A method of treating inflammation comprising administering to a human or animal patient in need of said treatment, an effective amount of a compound as defined in claim 13.

29. A method of treating colorectal cancer comprising administering to a human or animal patient in need of said treatment, an effective amount of a compound as defined in any one of claims 1 to 7.

30. A method of treating colorectal cancer comprising administering to a human or animal patient in need of said treatment, an effective amount of a compound as defined in claim 8.

31. A method of treating colorectal cancer comprising administering to a human or animal patient in need of said treatment, an effective amount of a compound as defined in claim 9.

32. A method of treating colorectal cancer comprising administering to a human or animal patient in need of said treatment, an effective amount of a compound as defined in claim 13.

33. A method of treating conditions mediated by prostanoid-induced smooth muscle contraction comprising administering to a human or animal patient in need of said treatment, an effective amount of a compound as defined in any one of claims 1 to 7.

34. A method of treating conditions mediated by prostanoid-induced smooth muscle contraction comprising administering to a human or animal patient in need of said treatment, an effective amount of a compound as defined in claim 8.

35. A method of treating conditions mediated by prostanoid-induced smooth muscle contraction comprising administering to a human or animal patient in need of said treatment, an effective amount of a compound as defined in claim 9.

36. A method of treating conditions mediated by prostanoid-induced smooth muscle contraction comprising administering to a human or animal patient in need of said treatment, an effective amount of a compound as defined in claim 13.

37. A method of inhibiting prostanoid-induced smooth muscle contraction comprising administering to a human or animal patient in need of said inhibiting effect, an effective amount of a compound as defined in any one of claims 1 to 7.

38. A method of inhibiting prostanoid-induced smooth muscle contraction comprising administering to a human or animal patient in need of said inhibiting effect, an effective amount of a compound as defined in claim 8.

39. A method of inhibiting prostanoid-induced smooth muscle contraction comprising administering to a human or animal patient in need of said inhibiting effect, an effective amount of a compound as defined in claim 9.

40. A method of inhibiting prostanoid-induced smooth muscle contraction comprising administering to a human or animal in need of said inhibiting effect, patient an effective amount of a compound as defined in claim 13.

41. A 3,4-diaryloxazolone compound of formula (XIV):

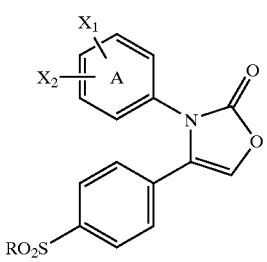

(XIV)

wherein:
R is:
    a lower alkyl radical having 1 to 6 carbon atoms, or
A is:
    a phenyl ring,
$X_1$, and $X_2$ independently are:
    the hydrogen atom,
    a halogen atom,
    a lower alkyl radical having 1 to 6 carbon atoms, or
    a trifluormethyl radical.

42. A compound of formula (XIV) according to claim 41, wherein:
R is a lower alkyl radical having 1 to 6 carbon atoms,
A is a phenyl ring,
$X_1$ and $X_2$ independently are:
    the hydrogen atom,
    a fluorine atom and a chlorine atom,
    a lower alkyl radical having 1 to 6 carbon atoms, or
    a trifluoromethyl radical.

43. A compound according to claim 41 wherein R is the methyl radical.

44. A compound according to claim 41 wherein $X_1$ is selected from the group consisting of the fluorine atom, the chlorine atom and a methyl radical and $X_2$ is the hydrogen atom.

45. A compound according to claim 41 wherein $X_1$ and $X_2$ are the chlorine atom.

46. A compound according to claim 41 which is selected from the group consisting of:
3-(4-fluorophenyl)-4-(4-methanesulfonylphenyl)-3H-oxazol-2-one

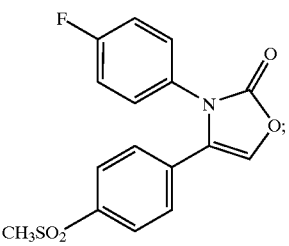

3-(4-chlorophenyl)-4-(4-methanesulfonylphenyl)-3-H-oxazol-2-one

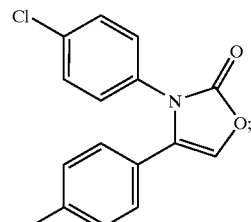

3-(3-methylphenyl)-4-(4-methanesulfonylphenyl)-3H-oxazol-2-one

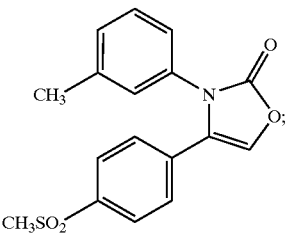

3-(3-chlorophenyl)-4-(4-methanesulfonylphenyl)-3H-oxazol-2-one

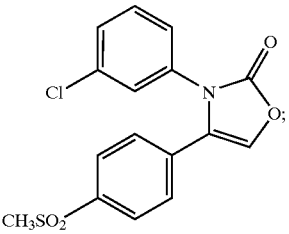

and
3-(3,4-dichlorophenyl)-4-(4-methanesulfonylphenyl)-3H-oxazol-2-one

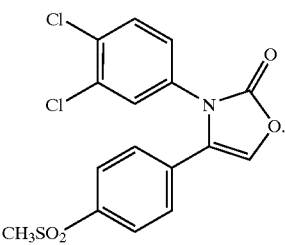

47. A pharmaceutical composition which comprises a pharmaceutically effective amount of a compound of formula (XIV) as defined in claim 41 incorporated in a pharmaceutically acceptable excipient, vehicle or carrier.

48. A pharmaceutical composition with anti-inflammatory and analgesic activity which comprises a pharmaceutically effective amount of a compound of formula (XIV) as defined in claim 41 incorporated in a pharmaceutically acceptable excipient, vehicle or carrier.

49. A pharmaceutically acceptable composition according to claim 47 which is presented in the form of gelatin capsules or tablets containing a dose of between 1 mg to 1,000 mg or between 10 mg and 500 mg.

50. A pharmaceutically acceptable composition according to claim 47 which is presented in the form of injectable preparations containing a dose of 0.1 mg to 500 mg.

51. A method for the treatment of inflammation in a mammal which comprises administering an effective amount of a compound of formula (XIV) as defined in claim 41 to the said mammal.

52. A method for the treatment of pain in a mammal which comprises administering an effective amount of a compound of formula (XIV) as defined in claim 41 to the said mammal.

* * * * *